United States Patent [19]

Sayo et al.

[11] Patent Number: 5,206,399
[45] Date of Patent: Apr. 27, 1993

[54] 2,2'-BIS(DIPHENYLPHOSPHINO)-5,5',6,6',7,7',8,8'-OCTAHYDRO-1,1'-BINAPHTHYL AND TRANSITION METAL COMPLEX CONTAINING THE SAME AS LIGAND

[75] Inventors: Noboru Sayo; Hidenori Kumobayashi, both of Tokyo, Japan

[73] Assignee: Takasago International Corporation, Tokyo, Japan

[21] Appl. No.: 769,264

[22] Filed: Oct. 1, 1991

[30] Foreign Application Priority Data

Oct. 1, 1990 [JP] Japan .................... 2-263440

[51] Int. Cl.⁵ .................... C07F 15/00; C07F 9/50
[52] U.S. Cl. .................... 556/20; 556/21; 556/136
[58] Field of Search .................... 556/136, 20, 21

[56] References Cited

U.S. PATENT DOCUMENTS 4,994,590 2/1991 Takaya et al. .................... 556/136 X Primary Examiner—Arthur C. Prescott
Attorney, Agent, or Firm—Sughrue, Mion, Zinn, Macpeak & Seas

[57] ABSTRACT 2,2'-Bis(diphenylphosphino)-5,5',6,6',7,7',8,8'-octahydro-1,1'-binaphthyl represented by formula (I).

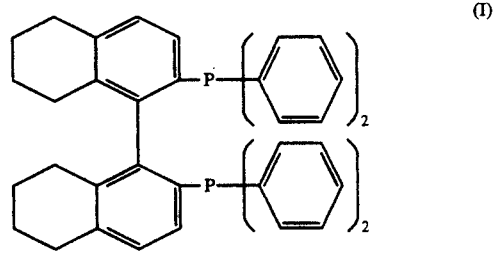

is disclosed. A transition metal complex containing the same, a process for producing 2,2'-Bis(diphenylphosphino)-5,5',6,6',7,7',8,8'-octahydro-1,1'-binaphthyl, and a process for producing 2,2'-bis(diphenylphosphinyl)-5,5',6,6',7,7',8,8'-octahydro-1,1'-binaphthyl are also disclosed.

6 Claims, No Drawings

2,2'-BIS(DIPHENYLPHOSPHINO)-5,5',6,6',7,7',8,8'-OCTAHYDRO-1,1'-BINAPHTHYL AND TRANSITION METAL COMPLEX CONTAINING THE SAME AS LIGAND

FIELD OF THE INVENTION

The present invention relates to a novel phosphine compound, more particularly, a novel phosphine compound which forms complexes with transition metals such as rhodium, ruthenium, iridium, palladium, and nickel, thereby providing catalysts useful in various enantioselective synthesis reactions. The invention further relates to such a transition metal complex containing the phosphine compound as a ligand, an intermediate for the phosphine compound, and a process for producing the intermediate.

BACKGROUND OF THE INVENTION

Hitherto, many reports have been made on transition metal complexes utilizable in organic synthesis reactions, for example, transition metal complex catalysts for use in enantioselective synthesis reactions such as enantioselective hydrogenation reaction, enantioselective isomerization reaction, and enantioselective silylation reaction. Among such transition metal complexes, most of the complexes in which optically active tertiary phosphine compounds are coordinated to transition metals such as ruthenium rhodium, and palladium show excellent efficiency when used as catalysts in enantioselective synthesis reactions. For the purpose of further enhancing the efficiency of this kind of catalysts, a large number of phosphine compounds having special structures have been developed so far [see *Kagaku Sosetsu* (The Elements of Chemistry) 32, "Chemistry of Organometallic Complexes" pp. 237–238 (1982), edited by The Chemical Society of Japan]. 2,2'-Bis(diphenylphosphino)-1,1'-binaphthyl (hereinafter referred to as "BINAP") is one of the phosphine compounds especially useful as a ligand, and a rhodium complex and a ruthenium complex each containing BINAP as a ligand have been reported in JP-A-55-61937 and JP-A-61-6390, respectively. (The term "JP-A" as used herein means an "unexamined published Japanese patent application".) It has also been reported that a rhodium complex (JP-A-60-199898) and a ruthenium complex (JP-A-61-63690) each containing 2,2'-bis[di-(p-tolyl)phosphino]-1,1'-binaphthyl (hereinafter referred to as "p-T-BINAP") as a ligand give good results when used in enantioselective hydrogenation reaction and enantioselective isomerization reaction. It has further been reported that the enantioselective hydrogenation reaction of nerol using as a catalyst a rhodium complex containing 2,2'-bis(dicyclohexylphosphino)-1,1'-binaphthyl (hereinafter referred to as "CyBINAP") as a ligand yields citronellol having an optical purity of 66% ee [S. Inoue et al., *Chemistry Letters*, pp. 1007–1008 (1985)].

As described above, a large number of special phosphine compounds have been developed in order to provide complexes which show higher catalytic efficiency when used in enantioselective synthesis reactions. However, there are cases where according to the kind of the reaction to be conducted or to the reaction substrate therefor, those complexes are still insufficient in selectivity, conversion, durability, and other performance. It has, therefore, been desired to develop a novel phosphine compound which gives complexes having significantly improved catalytic efficiency as compared with conventional catalysts.

SUMMARY OF THE INVENTION

In order to overcome the above-described problem, the present inventors have conducted intensive studies of many kinds of phosphine compounds. As a result, it has now been found that a transition metal complex containing as a ligand a novel phosphine compound obtained by replacing the binaphthyl group in BINAP by 5,5',6,6',7,7',8,8'-octahydrobinaphthyl group (bitetrahydronaphthalene group) is far more effective in improving selectivity and conversion in enantioselective syntheses than complexes containing BINAP, p-T-BINAP, and CyBINAP as ligands. The present invention has been completed based on this finding.

That is, the present invention provides 2,2'-bis-(diphenylphosphino)-5,5',6,6',7,7',8,8'-octahydro-1,1'-binaphthyl (hereinafter referred to as "OcH-BINAP") represented by formula (I):

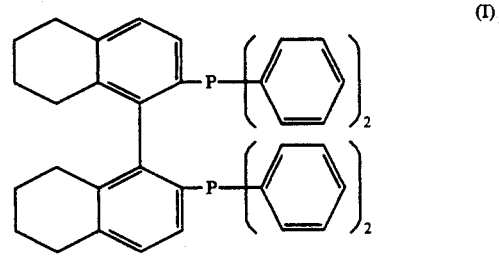

(I)

and a transition metal complex containing the above phosphine compound as a ligand. The present invention further provides a 5,5',6,6',7,7',8,8'-octahydro-1,1'-binaphthyl derivative which is an intermediate for OcH-BINAP and represented by formula (II):

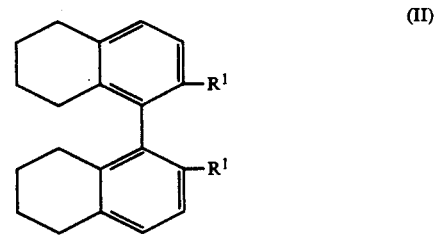

(II)

wherein $R^1$ represents a halogen atom, a halogenated magnesium, or

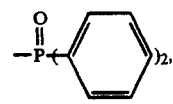

and a process for producing the above derivative.

DETAILED DESCRIPTION OF THE INVENTION

The novel compound, OcH-BINAP, according to the present invention includes optically active isomers, the (+)-isomer and the (−)-isomer, and any of the (+)-isomer, (−)-isomer, and racemate is included within the scope of this invention.

OcH-BINAP of the present invention can, for example, be produced according to the following reaction scheme, in which $X^1$ and $X^2$ each represents a halogen atom.

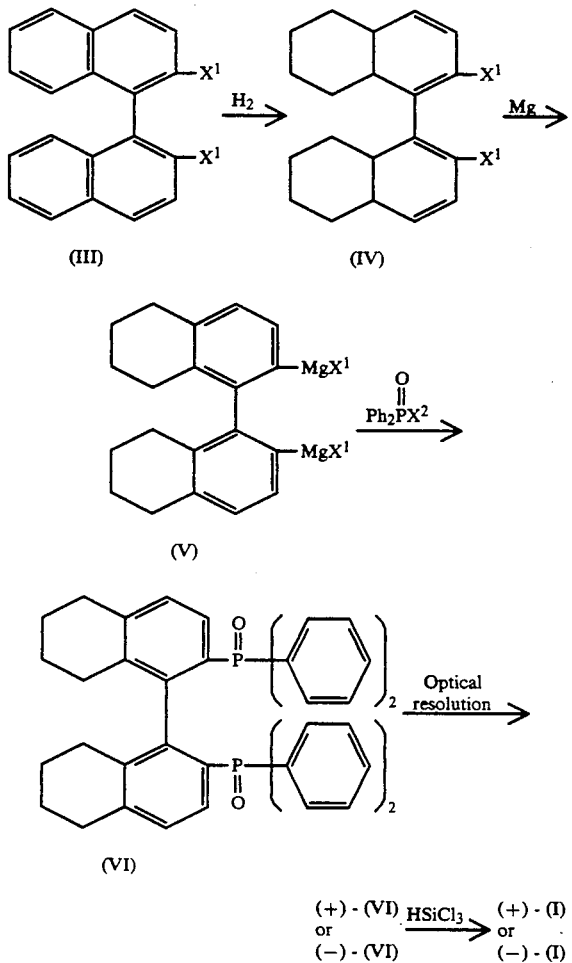

Illustratively stated, a 2,2'-dihalogeno-1,1'-binaphthyl (III) is hydrogenated in the presence of a ruthenium-on-carbon catalyst to give a 2,2'-dihalogeno-5,5',6,6',7,7',8,8'-octahydro-1,1'-binaphthyl (IV), which is then reacted with metallic magnesium to give a Grignard reagent (V). This Grignard reagent (V) is condensed with a diphenylphosphinyl halide to obtain 2,2'-bis(diphenyl-phosphinyl)-5,5',6,6',7,7',8,8'-octahydro-1,1'-binaphthyl (VI). As the starting material (III), 2,2'-dibromo-1,1'-binaphthyl can be synthesized according to the method proposed by H. Takaya et al. [J. Oro. Chem., 51, 629 (1986)]. The hydrogenation of this compound (III) may be conducted at a hydrogen pressure of 50 to 150 kg/cm² and a temperature of 70° to 120° C. for 15 to 25 hours in the presence of a ruthenium-on-carbon catalyst.

The reaction between the compound (IV) and metallic magnesium and the reaction of the thus-obtained Grignard reagent (V) with the diphenylphosphinyl halide may be performed according to ordinary Grignard reactions.

The racemate (VI) is reacted with an optically active dibenzoyltartaric acid as a resolving agent and recrystallized from a chloroform-ethyl acetate mixed solvent. The crystals deposited are collected by filtration and then treated with 1N sodium hydroxide to obtain a phosphine oxide. Recrystallization of this diastereomer is repeated until it becomes optically pure, while its optical purity is being determined by high-speed liquid chromatography employing an optically active column ("Chiralcel OG", manufactured by Daicel Chemical Industries, Ltd., Japan). Optical resolution by means of (−)-dibenzoyltartaric acid results in deposition of the (−)-isomer of compound (VI) as a diastereomer, while optical resolution by means of (+)-dibenzoyltartaric acid results in deposition of the (+)-isomer of compound (VI) as a diastereomer.

Finally, by reducing the thus-obtained (−)-(VI) or (+)-(VI) with trichlorosilane by a known method, the (+)-isomer or (−)-isomer of OcH-BINAP according to the present invention can be obtained.

As a ligand, the thus-obtained OcH-BINAP of the present invention forms a complex with a transition metal. Examples of such a transition metal forming the above complex include rhodium, palladium, ruthenium, -iridium, and nickel. Specific examples of the above complex include the following, in which COD represents 1,5-cyclooctadiene, Et represents ethyl group, and Ac represents acetyl group. (These abbreviations apply to the following description.)

[Rh(COD)(OcH-BINAP)]ClO₄
[Rh(COD)(OcH-BINAP)]PF₆
[Rh(COD)(OcH-BAINAP)]BF₄
Rh(COD)(OcH-BINAP)Cl
Rh(CO)(OcH-BINAP)Cl
PdCl₂(OcH-BINAP)
Ru₂Cl₄(OcH-BINAP)₂(NEt₃)
Ru(OAc)₂(OcH-BINAP)
[RuI(p-Cymene)(OcH-BINAP)]I
[RuCl(C₆H₆)(OcH-BINAP)]Cl
[Ir(COD)(OcH-BINAP)]BF₄
[Ir(COD)(OcH-BINAP)]PF₆
[Ir(COD)(OcH-BINAP)]ClO₄
NiCl₂(OcH-BINAP)

These transition metal complexes can, for example, be produced in the same manner as the synthesis method reported in J. A. Osborn et al., J. Am. Chem. Soc., 93, pp. 2397–2407 (1971) which method is for producing [Rh(COD)(dppe)]ClO₄ ("dppe"0 means 1,2-bis(diphenylphosphino)ethane).

That is, according to the method reported by J. A. Osborn et al. [J. Am. Chem. Soc., 93, p. 3089 (1971)], [Rh(COD)₂]ClO₄ synthesized from [Rh(COD)Cl]₂, COD, and AgClO₄ is reacted with OcH-BINAP of this invention to obtain 1,5-cyclooctadiene-[2,2'-bis(diphenylphosphino)-5,5',6,6',7,7',8,8'-octahydro-1,1'-binaphthyl]rhodium perchlorate, [Rh(COD)(OcH-BINAP)]ClO₄.

Alternatively, commercially available 1,5-cyclooctadienedi-μ-chlorodirhodium, [Rh(COD)Cl]₂, is reacted with OcH-BINAP according to the present invention in methylene chloride to obtain 1,5-cyclooctadiene-[2,2'-bis(diphenylphosphino)-5,5',6,6',7,7',8,8'-octahydro-1,1'-binaphthyl]rhodium chloride, Rh(COD)(OcH-BINAP)Cl.

In still another method, commercially available [Rh(CO)₂Cl]₂ is reacted with OcH-BINAP of the present invention at room temperature in methylene chloride in the same manner as the method reported in G. Wilkinson, Inorg. Synth., 8, pp. 214–217 (1966) which method is for synthesizing Rh(CO)Cl(PPh₃)₂ (Ph means phenyl group), thereby to obtain carbonyl-[2,2'-bis(diphenylphosphino)-5,5',6,6',7,7',8,8'-octahydro-1,1'- binaphthyl]rhodium chloride, Rh(CO)(OcH-BINAP)Cl.

In a further method, [RuCl$_2$(COD)]$_n$, which can easily be obtained from ruthenium chloride and COD, is reacted with OcH-BINAP of this invention with heating in toluene in the presence of triethylamine to obtain Ru$_2$Cl$_4$(OcH-BINAP)$_2$(NEt$_3$), in the same manner as the method for synthesizing Ru$_2$Cl$_4$(BINAP)$_2$(NEt$_3$) disclosed in T. Ikariya et al., *J. Chem. Soc., Chem. Commun.*, p. 922 (1985).

The thus-obtained transition metal complex according to the present invention, when used as a catalyst in an enantioselective synthesis reaction, for example, in the enantioselective hydrogenation reaction of a 2-(N-acylamino)methyl-3-oxobutanoic acid ester, shows high catalytic activity and gives the corresponding 2-(N-acylamino)methyl-3-hydroxybutanoic acid ester having a high optical purity and a high diastereoselectivity. When the transition metal complex is used as a catalyst for the enantioselective hydrogenation of geraniol or nerol, it shows high catalytic activity and gives citronellol in a high optical yield. Furthermore, when either the (−)-isomer or (+)-isomer of OcH-BINAP according to the present invention is selected to prepare a transition metal complex containing the selected isomer as a ligand and this complex is used as a catalyst in an enantioselective synthesis reaction, an intended compound having the desired absolute configuration can be obtained.

As described above, OcH-BINAP of the present invention can be an excellent ligand in catalysts for use in enantioselective synthesis. The complex of OcH-BINAP with a transition metal such as rhodium, ruthenium, iridium, or palladium shows excellent catalytic activity when used in various enantioselective syntheses such as enantioselective hydrogenation, enantioselective isomerization, and enantioselective silylation. Therefore, by use of this transition metal complex, optically active compounds having high optical purities can be produced.

The present invention will be explained below in more detail by reference to the following examples, which should not be construed to be limiting the scope of the invention.

In the Examples, the following analysis and measurements were conducted using apparatus specified below.

NMR: Model AM-400 (400 MHz) (manufactured by Bruker Inc.)
  Internal stardard: $^1$H-NMR ... tetramethylsilane
  External standard: $^-$P-NMR ... 85% phosphoric acid Optical Rotation: Model DIP-4 (manufactured by JASCO Inc., Japan)

Optical Purity: High-speed liquid chromatography, Model L-6000 (manufactured by Hitachi, Ltd., Japan)
  Detector UV detector L-4000UV (manufactured by Hitachi, Ltd.)
  Column: Chiralcel OG (manufactured by Daicel Chemical Industries, Ltd.)
  Eluent: hexane/isopropyl alcohol=90/10 by volume
  Flow rate: 1 ml/min
  Detection: UV 254 nm Chemical Purity: High-speed liquid chromatography, Model L-6000 (manufactured by Hitachi,Ltd.)
  Detector: UV detector L-4000UV (manufactured by Hitachi, Ltd.)
  Column: Cosmosil 5SL (manufactured by Nacalai tesque, Inc.)
  Eluent: hexane/isopropyl alcohol=90/10 by volume
  Flow rate: 1 ml/min
  Detection: UV 254 nm

EXAMPLE 1

(1) Synthesis of 2,2'-dibromo-5,5',6,6',7,7',8,8'-octahydro-1,1'-binaphthyl (IV):

Into a 500-ml stainless steel-made autoclave were introduced 35 g (0.085 mole) of 2,2'-dibromo-1,1'-binaphthyl (III), 5.25 g of 5%-ruthenium-on=carbon (manufactured by NECHEM CAT Inc.), 130 ml of ethyl acetate, and 130 ml of 95% ethanol. Hydrogenation was conducted at a hydrogen pressure of 50 kg/cm$^2$ and a temperature of 100° C. for 20 hours, and it was then ascertained that the molar amount of hydrogen absorbed by the substrate had become four times that of the substrate. Thereafter, the reaction mixture was cooled to 30° C. and filtered to remove the catalyst. The resulting filtrate was allowed to stand at room temperature for a night, and crystals deposited were then collected by filtration. Thus, 30.6 g of the titled compound (IV) was obtained.

Percent yield 85.7%, Melting point 146°–147° C.
$^1$H-NMR (CDCl$_3$) δ ppm:
1.75 (m, 8H), 2.08 (dt, 2H, J=17.67 Hz), 2.33 (dt, 2H, J=17.67 Hz), 2.77 (m, 4H), 6.98 (d, 2H', J=8.2 Hz), 7.42 (d, 2H, J=8.2 Hz).

(2) Synthesis of 2,2'-bis(diphenylphosphoryl)-5,5',6,6',7,7',8,8'-octahydro-1,1'-binaphthyl (VI)

Into a 1-liter four-necked flask was placed 4.26 g (0.177 mole) of magnesium. After nitrogen replacement, a small amount of iodine and 20 ml of dry tetrahydrofuran were added in this order. Thereto was then added 0.6 ml of 1,2-dibromoethane using a syringe. To the mixture in the flask, a solution separately prepared by dissolving 32.5 g (0.0774 mole) of 2,2'-dibromo-5,5',6,6',7,7',8,8'-octahydro-1,1,-binaphthyl (IV) in a mixed solvent of 330 ml of toluene and 90 ml of tetrahydrofuran was added dropwise from a dropping funnel over a period of 7 hours. During this addition, the temperature of the reaction mixture was 80° to 90° C. After the addition of the compound (IV) solution, stirring was further continued at 94° C. for 19 hours. The resulting reaction mixture was cooled to 5° C., and 34.27 g (0.148 mole) of diphenylphosphinic chloride was added thereto dropwise over a period of 30 minutes. The reaction mixture was then heated to 72° C., stirred at this temperature for 3.5 hours, and then cooled to room temperature. Thereafter, 100 ml of water was added thereto, and the resulting mixture was heated to 80° C., stirred at this temperature for 20 minutes, cooled to room temperature, and then allowed to stand for a night, whereby a white solid was deposited. This solid was collected by filtration, washed twice with 100 ml of water, further washed with 100 ml of a hexane-toluene (9:1 by volume) mixture, and then dried under a reduced pressure (0.1 mmHg) at 70° C. for 7 hours, thereby obtaining 32.8 g of the titled compound (VI).

Percent yield 64.1%, Melting- point 300° C. (decomposed).
$^1$H-NMR (CDCl$_3$) δ ppm:

6.938 (d, 1H, J=13.29 Hz), 6.958 (d, 1H, J=13.29 Hz), 7.002 (d, 1H, J=3.19 Hz), 7.022 (d, 1H, J=3.19 Hz), 7.36 (m, 4H), 7.43 (m, 4H), 7.51 (tq, 4H), 7.65 (dp, 4H), 7.78 (dp, 4H).
$^{31}$P-NMR (CDCl$_3$) δ ppm: 28.415.

(3) Optical resolution of 2,2'-bis(diphenylphosphinyl)-5,5',6,6',7,7',8,8'-octahydro-1,1'-binaphthyl (VI)

In 2,000 ml of heated chloroform was dissolved 90 g (11.62 mmole) of phosphine oxide of the racemate (VI). Separately, 47.69 g (13.31 mmole) of (−)-dibenzoyltartaric acid was dissolved in 1,300 ml of ethyl acetate at 70° C. Both solutions were mixed with stirring. The resulting mixture was allowed to stand at room temperature for a night, and crystals deposited were collected by filtration and dried under a reduced pressure (0.1 mmHg) at room temperature for 10 hours, thereby obtaining 57.94 g of a salt. This salt was dissolved again with stirring in a mixed solvent of 700 ml of chloroform, 120 ml of ethanol, and 1,400 ml of ethyl acetate. The resulting solution was cooled to room temperature, whereby crystals were deposited. The crystals were collected by filtration and dried under a reduced pressure (0.1 mmHg) at room temperature to obtain 54.87 g of a salt. This salt was mixed with 1,000 ml of 1.5N sodium hydroxide, extracted three times with 1,000 ml of chloroform, washed with 400 ml of 1.5N sodium hydroxide, further washed three times with 1,000 ml of water, dried over anhydrous magnesium sulfate, and then concentrated. Thus, 32.48 g of an optically active isomer of compound (VI) was obtained. The percent yield was 44.21%.

[α]$_D^{24}$ −33.91° (c=0.5, CHCl$_3$).

On the other hand, 1,400 ml of 1.5N sodium hydroxide was added to the mother liquor resulting from the above resolution. Extraction was then conducted twice with 1,000 ml of chloroform. The extract was dried over anhydrous magnesium sulfate. To this chloroform solution was added a solution separately prepared by dissolving 28 g of (+)-dibenzoyltartaric acid in 200 ml of ethyl acetate at 70° C. The resulting mixture was allowed to stand at room temperature for a night. Crystals deposited were collected by filtration and then dissolved again in a mixed solvent of 700 ml of chloroform, 120 ml of ethanol, and 1,400 ml of ethyl acetate. Crystals deposited at room temperature were collected by filtration, mixed with 1,000 ml of 1.5N sodium hydroxide, extracted three times with 1,000 ml of chloroform, washed three times with 1,000 ml of water, dried over anhydrous magnesium sulfate, and then concentrated. Thus, 29.8 g of an optically active isomer of compound (VI) was obtained. The percent yield was 40.67%.

[α]$_D^{24}$ +34.66° (c=0.5, CHCl$_3$).

The optical purities of the above-obtained (−)-(VI) and (+)-(VI) were measured by high-speed liquid chromatography employing an optically active column (Chiralcel OG) and found to be 98.46% ee and 100% ee, respectively.

(4) Synthesis of optically active 2,2'-bis(diphenylphosphino)-5,5',6,6',7,7',8,8'-octahydro-1,1'-binaphthyl (I):

Into a 500-ml four-necked flask was placed 4.6 g (6.04 mmole) of (−)-(VI). After nitrogen replacement, 150 ml of xylene, 3.67 g (36.24 mmole) of triethylamine, and 4.91 g (36.24 mmole) of trichlorosilane were added thereto. This mixture was stirred at room temperature for 20 minutes, at 90 to 110° C. for 20 minutes, at 110° to 120° C. for 1 hour, and then at 130° C. for 16.5 hours. To the reaction mixture were then added 1.88 g (13.88 mmole) of trichlorosilane and 1.38 g (13.64 mmole) of triethylamine. The resulting mixture was stirred at 130° C. for 6 hours and then cooled to room temperature. Subsequently, 100 ml of 3N sodium hydroxide was added, and the resultant mixture was stirred at 60° C. for 2 hours and then cooled to room temperature. The resulting organic layer was separated from the aqueous layer, dried over anhydrous magnesium sulfate, and then concentrated, thereby obtaining 3.49 g of (−)-(I). The percent yield was 91.7%.

[α]$_D^{24}$ −72.42° (c=0.504, toluene).
Melting point 207°–208° C.
$^1$H-NMR (CDCl$_3$) δ ppm:
0.890 (m, 2H), 1.27 (m, 2H), 1.45 (m, 4H), 1.54 (dt, 2H), 1.84 (dq, 2H), 2.64 (dt, 2H), 2.71 (dt, 2H), 6.88 (dt, 2H), 7.03 (d, 2H), 7.20 (brs, 10H), 7.30 (m, 10H).
$^{31}$P-NMR (CDCl$_3$) δ ppm: −15.3374.
Elemental analysis for C$_{44}$H$_{40}$P$_2$Rh:
Calculated: C:83.79% H:6.39%;
Found: C:83.51% H:6.38%.

Using (+)-(VI), (+)-(I) was obtained in the same manner as the above.
[α]$_D^{24}$ +72.35° (c=0.516, toluene).
Melting point 207°–208° C.
The $^1$H-NMR data for (+)-(I) were identical with the above $^1$H-NMR data for (−)-(I).

EXAMPLE 2

In 3 ml of methylene chloride were dissolved 0.4107 g (0.652 mmole) of (−)-OcH-BINAP (I) as obtained in Example 1-(4) and 0.225 g (0.537 mmole) of [Rh(COD)$_2$]ClO$_4$ synthesized according to the method proposed by J. A. Osborn et al. The reactants in the solution were reacted at room temperature for 30 hours. The resulting reaction mixture was concentrated to 1.5 ml, and 6 ml of diethyl ether was gradually added thereto. Crystals deposited were collected by filtration, washed with 3 ml of diethyl ether, and then dried. There was thus obtained 0.48 g of 1,5-cyclooctadiene-[2,2'-bis(diphenylphosphino)-5,5',6,6',7,7',8,8'-octahydro-1,1'-binaphthyl]rhodium perchlorate, [Rh(COD)((−)-OcH-BINAP)]ClO<. The percent yield was 95%.
$^{31}$P-NMR (CDCl$_3$) δ ppm:-25.01.
Elemental analysis for C$_{52}$H$_{52}$ClO$_4$P$_2$Rh:
Calculated: C 66.35% H:5.57%;
Found: C:65.97% H:5.49%.

EXAMPLE 3

Into a 50-ml multi-necked eggplant flask were placed 53 mg (0.136 mmole) of [Rh(CO)$_2$Cl]$_2$ (manufactured by Aldrich Inc.) and 174 mg (0.276 mmole) of (−)-OcH-BINAP as obtained in Example 1-(4). After nitrogen replacement, 5 ml of methylene chloride was added, and the mixture was stirred at room temperature for 2 hours. The resulting insoluble matter was removed by filtration, and the filtrate was concentrated and dried, thereby obtaining 0.206 g of carbonyl-[2,2'-bis(diphenylphosphino)-5,5',6,6',7,7',8,8'-octahydro-1,1'-binaphthyl]rhodium chloride, [Rh(CO)((−)-OcH-BINAP)]Cl. The percent yield was 95.1%.
$^1$H-NMR (CDCl$_3$) δ ppm:
1.05–2.50 (m, 16H), 6.60–7.90 (m, 24H).
$^{31}$P-NMR (CDCl:) δ ppm:

22.44 (dd), 45.75 (dd).
IR (KBr): 2005 cm$^{-1}$ (strong).
Elemental analysis for $C_{45}H_{40}ClOP_2Rh$:
Calculated: C:67.81% H:5.06%;
Found: C:67.2% H:4.98%.

EXAMPLE 4

Into a 100-ml multi-necked flask were placed 0.189 g (0.3 mmole) of (+)-OcH-BIN-AP, 0.15 g (0.6 mmole) of [Rh(COD)Cl]$_2$ (manufactured by Strem Chemicals Inc.), 0.200 g (1.8 mmole) of NaBF°, 0.013 g (0.06 mmole) of $(C_2H_5)_4NBr$, 30 ml of methylene chloride, and 20 ml of water. The reactants were then reacted at 5° to 10° C. for 1.5 hours. The methylene chloride was then separated from the resulting reaction mixture and washed three times with 20 ml of water for each washing. The resulting methylene chloride solution was concentrated to dryness, thereby obtaining 0.279-g of 1,5-cyclooctadiene-[2,2'-bis(diphenylphosphino)-5,5',6,6',7,7',8,8'-octahydro-1,1'-binaphthyl]rhodium tetrafluoroborate, [Rh(COD)((+)-OcH-BINAP)]BF$_4$.

Elemental analysis for $C_{52}H_{52}BF_4P_2Rh$:
Calculated: C:67.26% H:5.64%;
Found: C:67.31% H:5.58%.

EXAMPLE 5

Into a 300-ml multi-necked flask were placed 0.236 g (0.241 mmole) of [RuI$_2$(p-Cymene)]$_2$ synthesized by the method proposed by K. Mashima et al. [*J. Chem. Soc., Chem. Commun.*, p. 1208 (1989)]and 0.3035 g (0.481 mmole) of (−)-OcH-BINAP as obtained in Example 1-(4). After nitrogen replacement, 16 ml of methylene chloride was added, and the mixture was stirred at 40° C. for 2 hours. The methylene chloride was then removed by evaporation, and the residue was dried under a reduced pressure (0.1 mmHg) at room temperature for 15 hours. There was thus obtained 0.58 g of iodo-π-p-cymene-[2,2'-bis(diphenylphosphino)-5,5',6,6',7,7',8,8'-,-octahydro-1,1'-binaphthyl]ruthenium iodide, [RuI(p-Cymene)((−)-OcH-BINAP)]I, was obtained. The percent yield was quantitative.

$^{31}$P-NMR (CDCl$_3$) δ ppm:
23.2418(d), 39.7730(d).
Elemental analysis for $C_{54}H_{54}I_2P_2Ru$:
Calculated: C:57.92% H:4.86%;
Found: C:56.66% H:4.80%.

EXAMPLE 6

Into a 200-ml multi-necked flask were placed 0.985 g (3.38 mmole) of [Ru(COD)Cl$_2$]$_n$ synthesized by reacting ruthenium trichloride with 1,5-cyclooctadiene in ethanol according to the method proposed by M. A. Bonnett et al. [*Chem. & Ind.*, 1516 (1959)]and 2.40 g (3.81 mmole) of (−)-OcH-BINAP as obtained in Example 1-(4). After nitrogen replacement, 100 ml of toluene and 2 ml (14.35 mmole) of triethylamine were added, and the mixture was heated with refluxing at 115° C. for 15 hours. The resulting reaction mixture was cooled to 30° C., the toluene was removed by evaporation under a reduced pressure (2 mmHg), and the residue was then dried under a high vacuum (0.1 mmHg) for 10 hours. Thus, 3.25 g (percent yield: 100%) of tetrachlorodi[2,2'-bis(diphenylphosphino)-5,5',6,6',7,7',8,8'-octahydro-1,1'-binaphthyl]diruthenium triethylamine, Ru$_2$Cl$_4$((−)-OcH-BINAP)$_2$(NEt$_3$), was obtained. The percent yield was quantitative.

$^{31}$P-NMR (CDCl$_3$) δ ppm:
44.78 (d), 51.34 (d).

Elemental analysis for $C_{94}H_{95}Cl_4NP_4Ru_2$:
Calculated: C:66.16% H:5.61%;
Found: C:67.03% H:5.78%.

EXAMPLE 7

Into a 200-ml multi-necked flask were placed 1.94 g (1.14 mmole) of Ru$_2$Cl$_4$((−)-OcH-BINAP)$_2$(NEt$_3$) as obtained in Example 6 and 0.984 g (12 mmole) of sodium acetate. After nitrogen replacement, 50 ml of tert-butanol was added, and the mixture was heated with refluxing at 85° C. for 10 hours. The resulting mixture was then cooled to 50° C., and the tert-butanol was removed by evaporation under a reduced pressure (20 mmHg) to obtain a dark-green solid. To this solid was added 30 ml of ethanol. The ethanol into which part of the solid had dissolved was taken out, 30 ml of ethanol was added again to the residue, and the resulting ethanol solution was then taken out. These ethanol solutions were gathered and concentrated to dryness. Subsequently, 8 ml of toluene was added thereto, and this mixture was heated with refluxing. The resulting toluene solution was separated from the insoluble matter and mixed with 16 ml of n-hexane. This solution was allowed to stand in a refrigerator for a night, and a solid substance deposited was collected by filtration and dried under a reduced pressure (0.1 mmHg) at room temperature. Thus, 1.48 g of [2,2'-bis(diphenylphosphino)-5,5',6,6',7,7',8,8'-octahydro-1,1'-binaphthyl]ruthenium diacetate, Ru(OAc)$_2$((−)-OcH-BINAP), was obtained. The percent yield was 76.4%.

$^{31}$P-NMR (CDCl$_3$) δ ppm: 64.18.
Elemental analysis for $C_{48}H_{46}O_4P_2Ru$:
Calculated: C:67.83% H:5.46%;
Found: C:67.98% H:5.65%.

EXAMPLE 8

Into a 50-ml multi-necked flask was placed 0.64 g (1.36 mmole) of [Ir(COD)(CH$_3$CN)$_2$BF$_4$ synthesized according to the method proposed by M. Green et-al. [*J. Chem. Soc.*, (A) 2334 (1971)], followed by adding 15 ml of tetrahydrofuran. Thereto was then added 10 ml of a tetrahydrofuran solution containing 0.86 g (1.36 mmole) of (−)-OcH-BINAP as obtained in Example 1-(4). This mixture was stirred at room temperature for 30 minutes. The insoluble matter was removed by filtration, and the filtrate was added to 300 ml of diethyl ether. The resulting mixture was allowed to stand at room temperature for 60 hours, and crystals deposited were collected by filtration and dried. Thus, 1.3 g of 1,5-cyclooctadiene-[2,2'-bis(diphenylphosphino)-5,5',6,6',7,7',8,8'-octahydro-1,1'-binaphthyl]iridium tetrafluoroborate, [Ir(COD)((−)-OcH-BINAP)]BF$_4$, was obtained. The percent yield was 93.9%.

$^{31}$P-NMR (CDCl$_3$) δ ppm: 14.9(s).
$^1$H-NMR (CDCl$_3$) δ ppm:
3.95 (m, 2H), 4.26 (m, 2H), 6.94 (d, 2H),;
7.32 (q, 4H), 7.40 (d, 2H), 7.54 (m, 16H).

EXAMPLE 9

Into a 100-ml multi-necked flask were placed 0.2 g (0.4 mmole) of [Ru(C$_6$H$_6$)Cl$_2$]$_2$ synthesized by the method proposed by K. Mashima et al. [*J. Chem. Soc., Chem. Commun.*, p. 1208 (1989)]and 0.505 g (0.8 mmole) of (−)-OcH-BINAP as obtained in Example 1-(4). After nitrogen replacement, 90 ml of ethanol and 12 ml of benzene were added, and this mixture was stirred at 50° C. for 45 minutes. The insoluble matter was removed by filtration, and the filtrate was concentrated. There was thus obtained 0.62 g of chloro n-benzene-[2,2'-bis(diphenylphosphino)-5,5',6,6',7,7',8,8'-octahydro-1,1'-binaphthyl]ruthenium chloride, [RuCl(C$_6$H$_6$)((−)-OcH-BINAP)]Cl. The percent yield was 87.9%.

$^1$H-NMR (CDCl$_3$) δ ppm:
0.95–2.60 (m, 16H), 5.59 (s, 6H), 6.06 (d, 1H), 6.89 (d, 1H), 7.15–7.43 (m, 6H), 7.48 (m, 8H), 7.72 (d, 1H).

$^{31}$P-NMR (CDCl$_3$) δ ppm: 28.14 (d), 37.19 (d).

APPLICATION EXAMPLE 1

Into a 200-ml stainless steel-made autoclave was placed 3.56 g (0.0143 mole) of methyl 2-benzamidomethyl-3-oxobutyrate. After nitrogen replacement, 7 ml of a separately prepared dichloromethane/methanol (7/1 by volume) mixed solvent solution containing 0.01 g (0.00894 mmole) of [RuI(p-Cymene)((−)-OcH-BINAP)]I as obtained in Example 5 was added. The resulting mixture was stirred at a hydrogen pressure of 50 kg/cm$^2$ and a temperature of 65° C. for 20 hours. After the reaction, the reaction mixture was analyzed by high-speed liquid chromatography. As a result, it was found that 2.79 g (percent yield: 78%) of methyl 2-benzamidomethyl-3-hydroxybutyrate had been formed and that the conversion was 80%, diastereomer selectivity 91.6%, and optical percent yield 99% ee.

APPLICATION EXAMPLE 2

Into a 200-ml stainless steel-made autoclave were placed 16.1 g (0.104 mmole) of geraniol, 17.7 mg (0.0208 mmole) of Ru(OAc)$_2$((−)-OcH-BINAP) as obtained in Example 7, and 18 ml of methanol. This mixture was stirred at a hydrogen pressure of 100 kg/cm$^2$ and a temperature of 25° C. for 5 hours. After completion of the reaction, the solvent was removed by evaporation, and the residual crude product was subjected to vacuum distillation using a Claisen distillation flask, thereby obtaining 15.89 g of citronellol. The percent yield was 98%, and the optical purity of the citronellol was 98.3% ee.

[α]$_D^{26}$ 5.11° (c=20.0, CHCl$_3$).

APPLICATION EXAMPLE 3

Into a 100-ml stainless steel-made autoclave was placed 206 mg (0.2 mmole) of [Ir(COD)((−)-OcH-BINAP)]BF$_4$ as obtained in Example 8. After nitrogen replacement, 2 ml of tetrahydrofuran/methanol (5/1 by volume) mixed solvent and 2.07 g (20.3 mmole) of 3-oxotetrahydrothiophene were added. The resulting mixture was stirred at a hydrogen pressure of 50 kg/cm$^2$ and a temperature of 30° C. for 45 hours. After completion of the reaction, the solvent was removed by evaporation, and the residual crude product was subjected to silica gel column chromatography (hexane/ethyl acetate 8/1 by volume) to separate the hydrogenation product from the unreacted starting compounds. Thus, 0.56 g of 3-hydroxytetrahydrothiophene was obtained.

[α]$_D^{24}$ −8.95° (c=2.0, CHCl$_3$).

The optical purity of this product was 62.1% ee, which was calculated based on the literature value of [α]$_D^{24}$ −14.6° (c=2, CHCl$_3$).

While the invention has been described in detail and with reference to specific embodiments thereof, it will be apparent to one skilled in the art that various changes and modifications can be made therein without departing from the spirit and scope thereof.

What is claimed is:

1. 2,2'-Bis(diphenylphosphino)-5,5',6,6',7,7',8,8'-octahydro-1,1'-binaphthyl represented by formula (I).

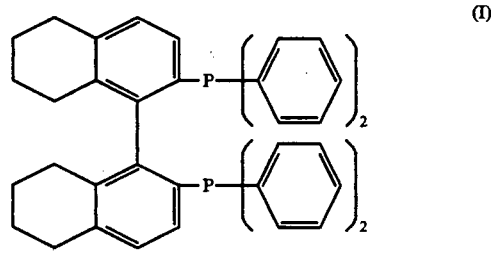

2. A transition metal complex comprising a transition metal and 2,2'-bis(diphenylphosphino)-5,5',6,6',7,7',8,8'-octahydro-1,1'-binaphthyl as a ligand.

3. A complex as in claim 2, wherein said transition metal is rhodium, ruthenium, or iridium.

4. A 5,5',6,6',7,7',8,8'-octahydro-1,1'-binaphthyl derivative represented by formula (II):

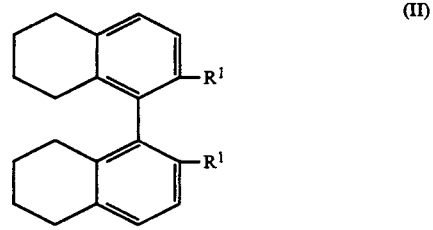

wherein R$^1$ represents a halogen atom, a halogenated magnesium, or

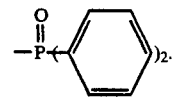

5. A process for producing a 2,2'-dihalogeno-5,5',6,6',7,7',8,8'-octahydro-1,1'-binaphthyl, which comprises hydrogenating a 2,2'-dihalogeno-1,1'-binaphthyl in the presence of a ruthenium-on-carbon catalyst.

6. A process for producing 2,2'-bis(diphenylphosphoryl)-5,5',6,6',7,7',8,8'-octahydro-1,1'-binaphthyl, which comprises hydrogenating a 2,2'-dihalogeno-1,1'-binaphthyl in the presence of a ruthenium-on-carbon catalyst and subsequently reacting the hydrogenation product with metallic magnesium and then with a diphenylphosphinyl halide.

* * * * *